(12) United States Patent
Wallenstein

(10) Patent No.: US 9,301,785 B2
(45) Date of Patent: Apr. 5, 2016

(54) SPINAL BUTTRESS PLATE

(75) Inventor: Todd Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 775 days.

(21) Appl. No.: 12/582,798

(22) Filed: Oct. 21, 2009

(65) Prior Publication Data

US 2010/0100131 A1  Apr. 22, 2010

Related U.S. Application Data

(60) Provisional application No. 61/107,115, filed on Oct. 21, 2008.

(51) Int. Cl.
*A61B 17/80* (2006.01)
*A61B 17/70* (2006.01)
*A61B 17/86* (2006.01)

(52) U.S. Cl.
CPC ........... *A61B 17/7059* (2013.01); *A61B 17/808* (2013.01); *A61B 17/809* (2013.01); *A61B 17/7074* (2013.01); *A61B 17/8635* (2013.01)

(58) Field of Classification Search
CPC ........... A61B 17/7059; A61B 17/8052; A61B 17/8057; A61B 17/808; A61B 17/8023
USPC ........... 606/70, 71, 280–284, 286–291, 86 A, 606/86 B
See application file for complete search history.

(56) References Cited

U.S. PATENT DOCUMENTS

| | | |
|---|---|---|
| 3,741,205 A | 6/1973 | Markolf et al. |
| 4,297,993 A * | 11/1981 | Harle ............ 606/70 |
| 5,085,660 A | 2/1992 | Lin |
| 5,147,361 A | 9/1992 | Ojima et al. |
| 5,180,381 A | 1/1993 | Aust et al. |
| 5,364,399 A | 11/1994 | Lowery et al. |
| 5,676,666 A | 10/1997 | Oxland et al. |
| 5,733,287 A | 3/1998 | Tepic et al. |
| 5,735,899 A | 4/1998 | Schwartz et al. |
| 5,904,683 A | 5/1999 | Pohndorf et al. |
| 6,159,213 A | 12/2000 | Rogozinski |
| 6,206,881 B1 | 3/2001 | Frigg et al. |
| 6,224,602 B1 | 5/2001 | Hayes |
| 6,228,085 B1 | 5/2001 | Theken et al. |
| 6,273,889 B1 | 8/2001 | Richelsoph |
| 6,306,136 B1 | 10/2001 | Baccelli |
| 6,306,139 B1 | 10/2001 | Fuentes |
| 6,309,393 B1 | 10/2001 | Tepic et al. |
| 6,322,562 B1 | 11/2001 | Wolter |
| 6,454,769 B2 | 9/2002 | Wagner et al. |
| 6,458,133 B1 | 10/2002 | Lin |
| 6,533,786 B1 | 3/2003 | Needham et al. |
| 6,595,993 B2 | 7/2003 | Donno et al. |
| 6,719,759 B2 | 4/2004 | Wagner et al. |
| 6,129,730 C1 | 5/2004 | Bono et al. |

(Continued)

*Primary Examiner* — Jan Christopher Merene
*Assistant Examiner* — Atiya Mahmud
(74) *Attorney, Agent, or Firm* — Carter, DeLuca, Farrell & Schmidt, LLP

(57) ABSTRACT

A spinal buttress plate includes a body having a top surface and a bottom surface and including an annular lip, a ledge, and a pair of teeth. The annular lip defines an opening. The annular lip and the opening are adapted to engage a screw for facilitating the securement of the buttress plate to one or more vertebrae. The ledge defines an aperture. The ledge and aperture are adapted to engage an instrument for positioning the buttress plate adjacent a spinal bone graft. The teeth are disposed in spaced-apart relation on the bottom surface of the body and are positionable within the one or more vertebrae.

17 Claims, 5 Drawing Sheets

(56) References Cited

U.S. PATENT DOCUMENTS

| | | |
|---|---|---|
| 6,755,832 B2 | 6/2004 | Happonen et al. |
| 6,884,242 B2 | 4/2005 | LeHuec et al. |
| 6,932,820 B2 | 8/2005 | Osman |
| 6,969,390 B2 | 11/2005 | Michelson |
| 6,989,012 B2 | 1/2006 | LeHuec et al. |
| 7,001,389 B1 | 2/2006 | Navarro et al. |
| 7,041,105 B2 | 5/2006 | Michelson |
| 7,048,739 B2 | 5/2006 | Konieczynski et al. |
| 2003/0225409 A1* | 12/2003 | Freid et al. ............ 606/69 |
| 2004/0019353 A1* | 1/2004 | Freid et al. ............ 606/69 |
| 2004/0127902 A1* | 7/2004 | Suzuki et al. .......... 606/69 |
| 2004/0204712 A1* | 10/2004 | Kolb et al. ............. 606/69 |
| 2005/0131420 A1* | 6/2005 | Techiera et al. ........ 606/99 |
| 2005/0234455 A1* | 10/2005 | Binder et al. ........... 606/69 |
| 2006/0100626 A1* | 5/2006 | Rathbun et al. ........ 606/69 |
| 2007/0088360 A1* | 4/2007 | Orbay et al. ........... 606/69 |
| 2007/0123884 A1* | 5/2007 | Abdou .................... 606/69 |
| 2008/0097435 A1* | 4/2008 | DeRidder et al. ...... 606/61 |
| 2008/0108998 A1* | 5/2008 | Lindemann ............ 606/71 |
| 2008/0234751 A1* | 9/2008 | McClintock ........... 606/291 |
| 2009/0012529 A1* | 1/2009 | Blain et al. ............ 606/99 |
| 2009/0036933 A1* | 2/2009 | Dube et al. ............ 606/282 |
| 2009/0076509 A1* | 3/2009 | Bush et al. ............. 606/71 |
| 2009/0143824 A1* | 6/2009 | Austin et al. .......... 606/280 |

\* cited by examiner

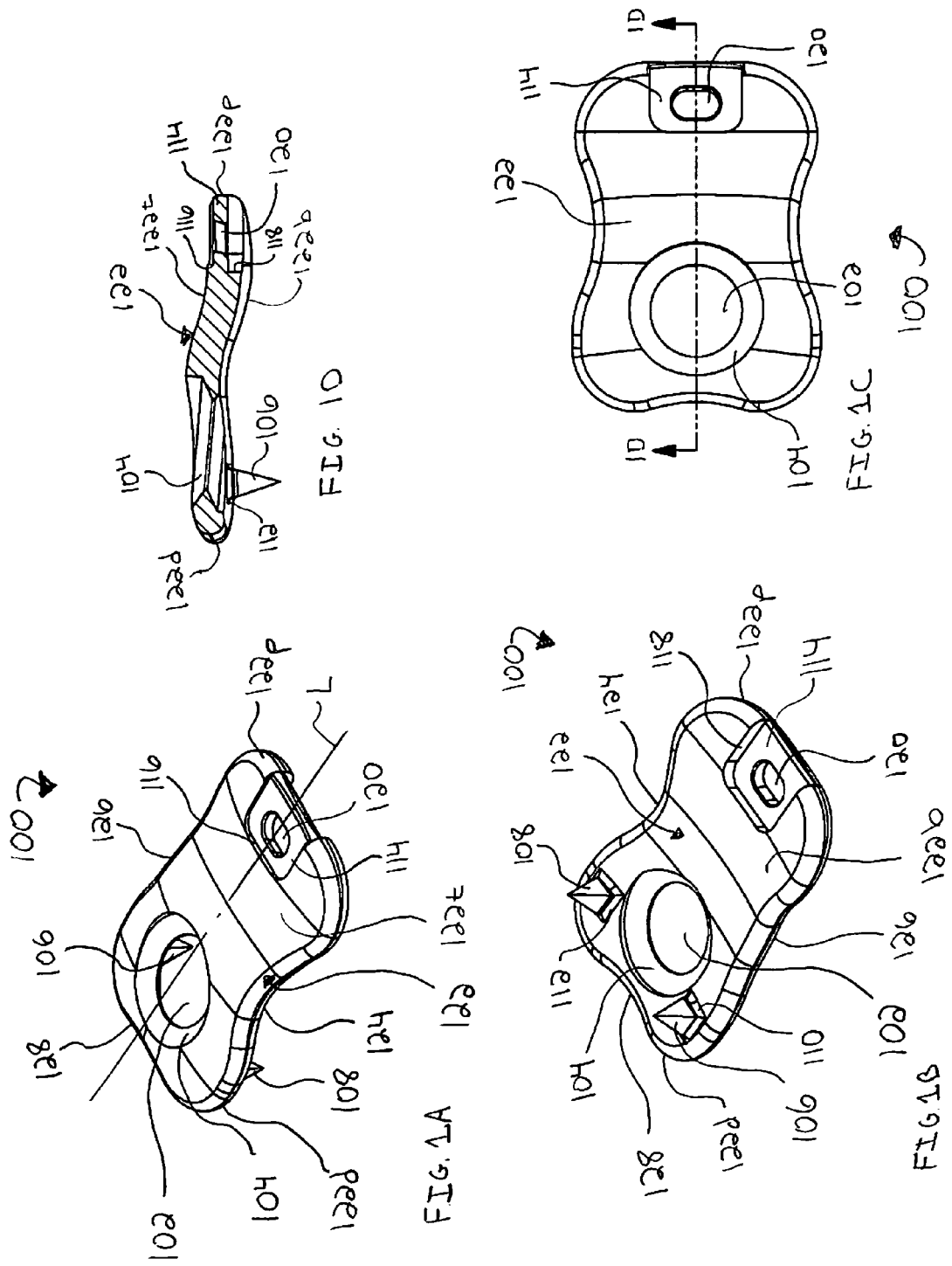

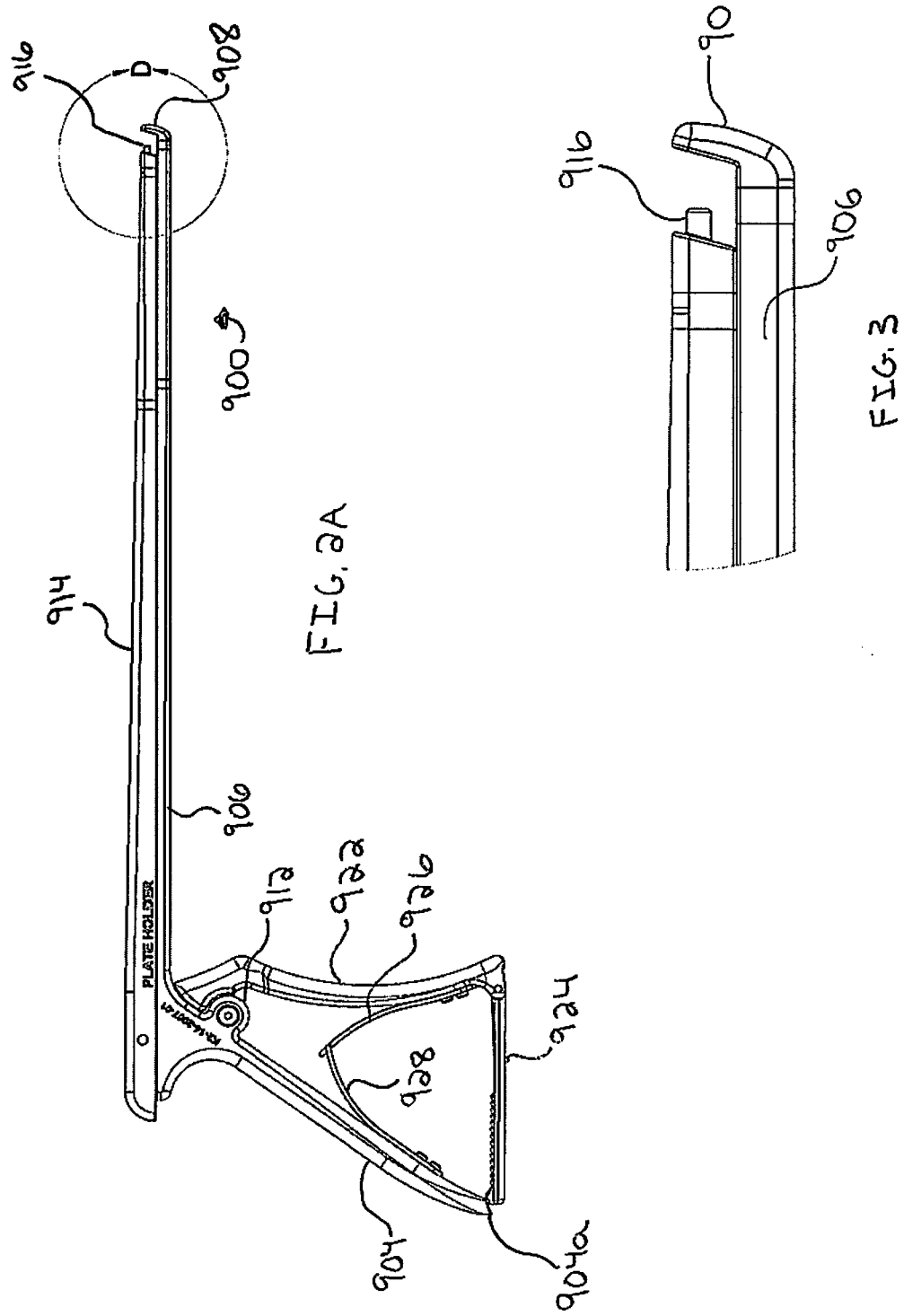

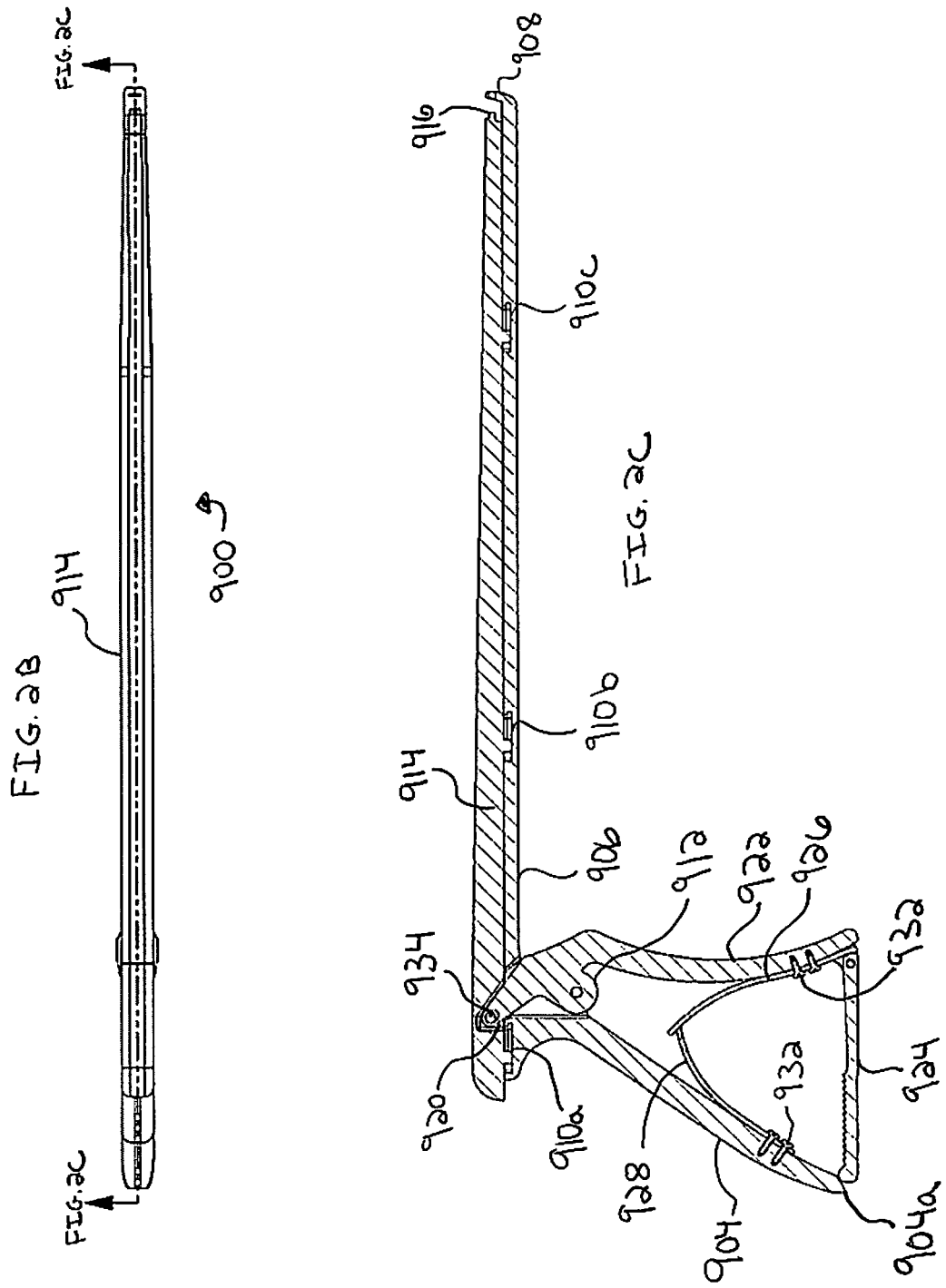

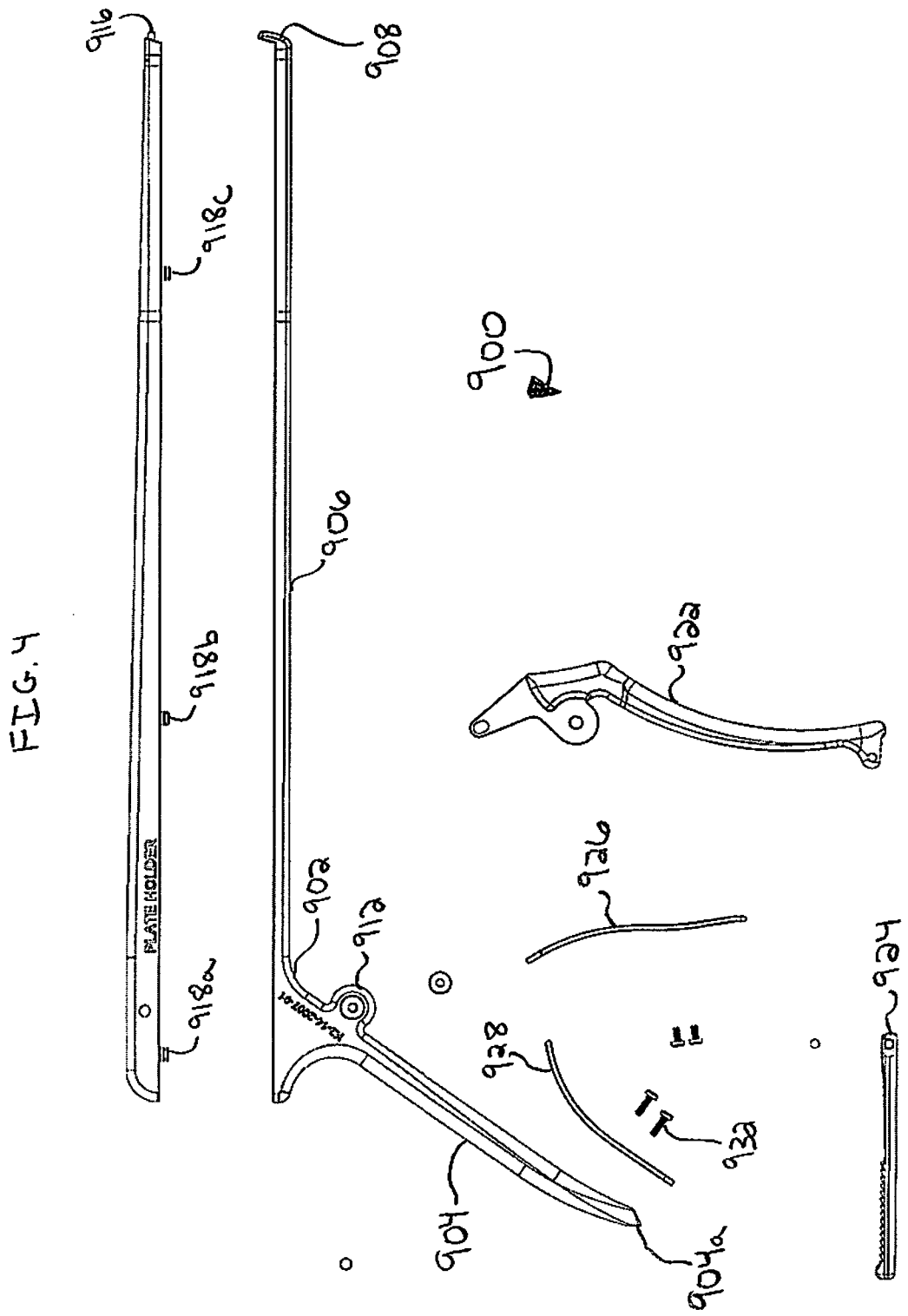

SPINAL BUTTRESS PLATE

CROSS REFERENCE TO RELATED APPLICATIONS

This application claims priority to, and the benefit of, U.S. Provisional Patent Application Ser. No. 61/107,115, filed Oct. 21, 2008, the contents of which are hereby incorporated by reference in their entirety.

BACKGROUND

1. Technical Field

The present disclosure relates generally to a spinal plate and, more particularly, to a spinal buttress plate for providing spinal bone graft support.

2. Background of Related Art

The human spinal column is a highly complex structure. It includes more than twenty discrete bones, known as vertebrae, coupled sequentially to one another to house and protect critical elements of the nervous system. Vertebrae, like any other bone, often fracture and require surgical reconstruction. Grafting materials such as autologous bone, allograft bone, xenograft, organic/inorganic material ("bone paste"), or other similar materials are commonly used in these procedures. These materials are used to promote bone healing as a biologic response and to provide structural support.

Intraarticular fractures are a common example of a situation in which grafting material can be used. The primary role of the grafting material is to buttress and/or support bone fragments in an anatomic or functional position. Additionally, the graft material may function to promote healing.

If the grafting material does not maintain its position at the site of application, several potential problems may occur. First and foremost, the material no longer functions for its intended purpose. Migration of graft material may lead to migration of the fragment to be supported. As a result, complications may arise such as joint incongruity, arthritis, stiffness, pain, crepitance with joint motion, non-union or malunion. Furthermore, secondary procedures (i.e. additional surgical procedures), may also be required.

In addition to losing intended function, migration of graft material may have additional deleterious effects. Migration of grafting material into adjacent soft tissues may initiate an inflammatory reaction or cause complications from mechanical pressure and irritation. For instance, graft material pressing on a nerve may cause nerve damage. Graft material pressing on tendons may cause fraying or rupture of the tendon or it may even cause scarring and limitation of tendon gliding. Migration of graft material into an adjacent joint can cause arthritis and joint damage. Moreover, the ability of grafting material to stimulate bone formation may cause problems if the graft migrates into the soft tissues. Occasionally, this may even stimulate formation of heterotopic bone in the soft tissues, which can cause scarring, stiffness, inflammation and pain.

Accordingly, a need exists for a spinal buttress plate that can be readily affixed to a vertebral body for protecting a vertebral bone graft.

SUMMARY

The present disclosure relates to a spinal buttress plate including a body having a top surface and a bottom surface and including an annular lip, a ledge, and a pair of teeth. The annular lip defines an opening. The annular lip and the opening are adapted to engage a screw for facilitating the securement of the buttress plate to one or more vertebrae. The annular lip may be formed of commercially pure titanium. The diameter of the annular lip increases as the surface of the annular lip approaches the top and bottom surfaces of the body. The annular lip may have a curvaceous surface. The material of the annular lip may be softer than the material of the screw such that the screw deforms the annular lip as the screw is secured thereto. The screw may be a self-tapping or a self-starting screw.

The ledge defines an aperture and may be disposed on either or both ends of the body. The ledge and aperture are adapted to engage an instrument for positioning the buttress plate adjacent a spinal bone graft.

The teeth are disposed in spaced-apart relation on the bottom surface of the body and are positionable within the one or more vertebrae. The teeth and the ledge are disposed on opposing ends of the body. One or both of the teeth are mounted to the body by a footing.

In one aspect, a method of attaching a buttress plate includes providing a buttress plate including a body having an annular lip defining an opening, a ledge defining an aperture, and a pair of teeth. The method includes providing an instrument having a rod and a prop extending therefrom adapted to support the buttress plate, mounting the rod within the aperture of the ledge, supporting the ledge against the prop of the instrument; positioning the buttress plate adjacent a superior vertebral body on one or both of the anterior or lateral sides of the spinal column over a bone graft, and securing one or more screws through the opening of the body of the buttress plate into the superior vertebral body. The method includes driving the pair of teeth into the superior vertebral body. The method may include deforming the annular lip with the at least one screw.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1A is a top perspective view of a spinal buttress plate in accordance with the present disclosure;

FIG. 1B is bottom perspective view of the spinal buttress plate set forth in FIG. 1A;

FIG. 1C is a top plan view of the spinal buttress plate of FIGS. 1A and 1B;

FIG. 1D is a cross-sectional view of FIG. 1C taken along section line 1D-1D;

FIG. 2A is a side view of a plate holder;

FIG. 2B is a top plan view of the plate holder of FIG. 2A;

FIG. 2C is a cross-sectional view of the plate holder of FIGS. 2A and 2B;

FIG. 3 is an enlarged view of the detailed area D of FIG. 2A;

FIG. 4 is an exploded view of the plate holder of FIGS. 2A and 2B;

DETAILED DESCRIPTION OF THE EMBODIMENTS

Figure 6:
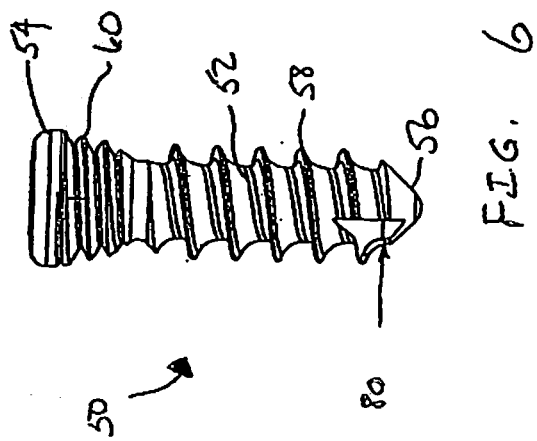
FIG. 6 is a side view of a self-tapping screw.

Various embodiments of the presently disclosed spinal buttress plate and system will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. In the following description, well-known functions or constructions are not described in detail to avoid obscuring the present disclosure in unnecessary detail.

Referring now to the drawings, in which like reference numerals identify identical or substantially similar parts throughout the several views, the spinal buttress plate shown in FIGS. 1A-1D is referred to generally as the plate 100. The plate 100 has a body 122, the body 122 including a pair of teeth (a first tooth 106 and a second tooth 108) disposed in spaced-apart relation on the underside thereof. The body 122 also has an opening 102 disposed on a distal end 122d thereof. The opening 102 has an annular lip 104. Additionally, the body 122 has a receiving ledge 114 disposed on a proximal end 122p thereof. The receiving ledge 114 has an aperture 120 whereby a plate holder 900 (FIG. 2A) can releasably grasp and position the plate 100 over a spinal bone graft. The first and second tooth 106, 108 are affixed to the body 122 via respective first and second footings 110, 112. The body 122 has first and second side notches 124, 126 and a top notch 128. The receiving ledge 114 is disposed at the proximal end 122p of the body 122 and is centrally positioned along a longitudinal axis "L" thereof. The receiving ledge 114 is offset a top and bottom distance from the respective top and bottom surfaces 122t, 122b of the body 122. The top distance is defined by the depth of a top side wall 116, while the bottom distance is defined by the depth of a bottom side wall 118. The length and width of the ledge 114 are defined to mesh with a prop 908 of a support arm 906 on a plate holder 900 (FIG. 2A). In other words, the ledge 114 is dimensioned to be releasably grasped by the plate holder 900. The aperture 120 is centrally disposed through the ledge 114. The aperture 120 is shaped to receive an engaging portion, such as a retaining rod 916 of a plate holder 900. In certain variations, the aperture is substantially elliptical or substantially circular. However, the aperture can be any polygonal shape.

Furthermore, the annular lip 104 of the opening 102 is defined by a pair of mirrored frustoconical cavities (see FIG. 1D) extending into the body 122 about the opening 102 from the top and bottom surfaces 122t, 122b. In other words, the diameter of the annular lip 104 increases as the surface of the annular lip 104 approaches the top and bottom surfaces 122t, 122b of the body 122. The annular lip 104 has the smallest diameter at the most central portion of the body 122 between the top and bottom surfaces 122t, 122b and the largest diameter at the top and bottom surfaces 122t, 122b of the body 122. The annular lip 104 may have a curvaceous surface. It is envisioned that the plate 100 is made from a relatively soft material such as commercially pure titanium or another suitable biocompatible material.

FIGS. 2A-2C and FIGS. 3-4 illustrate a plate holder 900. The plate holder 900 has a central assembly 902. The central assembly 902 has a handle 904 with a pawl end 904a, a support arm 906, and a pivot 912. The support arm 906 has a prop 908 disposed on the distal end thereof, while slide cavities 910a, 910b, 910c can be disposed therein in spaced-apart relation for receiving respective slides 918a, 918b, 918c extending from a shaft 914 having a retaining rod 916 disposed on the distal end thereof. A driving orifice 920 is disposed on the proximal end of the shaft 914 for receiving a drive bar 934 connected to the top portion of an actuator 922. The actuator 922 is pivotably connected to the central assembly 902 at the pivot 912. The actuator 922 is connected to a first bias bar 926 via screws 932. In addition, the actuator 922 and a ratchet 924 are connected at their respective distal ends. The first bias bar 926 and a second bias bar 928 are compressively connected at their respective distal ends. The second bias bar 928 is connected to the handle 904 of the central assembly 902 via screws 932.

Figure 5:
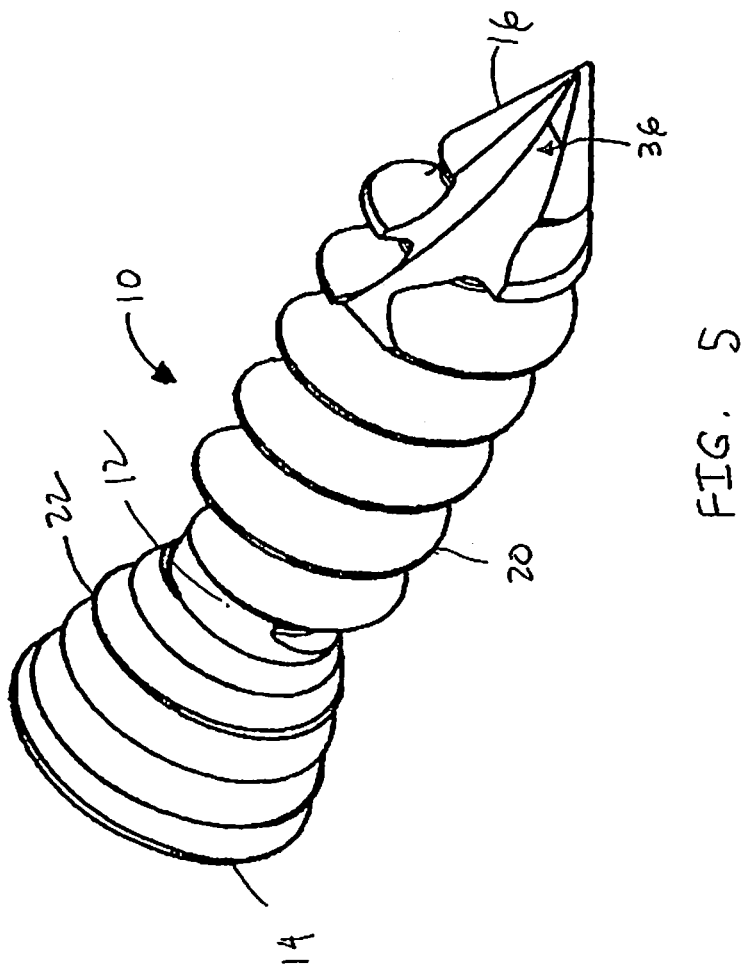
FIG. 5 is perspective view of a self-starting screw.

Referring now to FIGS. 5 and 6, a self-starting screw 10 and a self-tapping screw 50 are illustrated. The self-starting screw 10 has a shank 12, a tapered head portion 14 located at a proximal end of the shank 12 and a pointed tip portion 16 located at a distal end of the shank 12. The shank 12 has a uniform outer diameter and a first continuous helical thread 20 formed thereon. The first continuous helical thread 20 defines a cancellous bone thread. A second continuous thread 22 is formed on the head portion 14 and defines a thread thereon. The pitch of the first thread 20 is greater than the pitch of the second thread 22. Each of the threads 20, 22 has a uniform pitch. The self-starting screw 10 also includes a self-starting portion that extends proximally from the pointed tip portion 16. The self-starting portion includes first and second sidewalls that define a flute section 36. The first and second sidewalls of the flute section 36 extend from the pointed tip 16 to a second crest of cancellous bone thread 20.

The self-tapping screw 50 includes a shank 52, a tapered head portion 54 located at a proximal end of the shank 52, and a rounded tip portion 56 located at a distal end of the shank 52. The shank 52 has a uniform outer diameter and a first continuous helical thread 58 formed thereon. The first continuous helical thread 58 defines cancellous bone thread. A second continuous thread 60 is formed on the head portion 54 and defines a thread thereon. The pitch of the first thread 58 is greater than the pitch of the second thread 60. Each of the threads 58, 60 have a uniform pitch. The self-tapping screw 50 includes a self-tapping portion that extends proximally from the rounded tip portion 56. The self-tapping portion includes first and second sidewalls that define a flute section 80. The first and second sidewalls of the flute section 80 extend from the rounded tip 56 towards the second crest of cancellous bone thread 58. Each of the screws 10, 50 are formed from a suitable biocompatible material such as Ti-6AL-4V alloy. Alternatively, it is contemplated that other suitable biocompatible materials may be used to form the screws 10, 50.

Referring additionally to FIGS. 1A-1B and 5-6, the lip 104 is configured for engaging the screw 10, 50 such that rotating the screw 10, 50 causes the threads 22, 60 of the head 14, 54 of the respective screw 10, 50 to engage the lip 104 such that each screw 10, 50 is secured in the opening 102 and resists backing out of the screw opening 102. Since the material of the plate 100 is softer than the material of the screw 10, 50, the threads 22, 60 on the screw 10, 50 engage and deform the lip 104 as the screw 10, 50 is inserted into the opening 102, thereby securing the screw 10, 50 to the body 122. The threads 22, 60 of the screw 10, 50 engage the lip 104 when the screw 10, 50 is in various angular orientations with respect to the axis of the opening 102. A suitable screw and locking mechanism for use in the plate 100 are disclosed in U.S. Pat. No. 6,322,562 to Wolter, the entire contents of which are hereby incorporated by reference, although other mechanisms for locking the screw 10, 50 to the plate 100 are contemplated.

In operation, an end user affixes the plate holder 900 to the receiving ledge 114 of the buttress plate 100. Generally, the end user actuates the actuator 922 causing the drive bar 934 to drive the shaft 914 and rod 916 distally and the ratchet 924 to drive proximally. The ratchet teeth 930 cam under the pawl end 904*a* of the handle 904 as the end user continues to actuate the actuator 922. The rod 914 engages the aperture 120 from the top surface of the ledge 114 and locks the plate 100 to the prop 908 as the prop 908 engages the ledge 114 on the bottom surface of the ledge 114. Upon fully engaging the plate 100, the end user releases the actuator 922 and the pawl end 904*a* of the handle 904 locks into the ratchet teeth 930 of the ratchet 924 from the compression caused by the biasing of the first and second bias bars 926, 928, holding the plate 100 in locked position.

The end user then positions the plate 100 using the plate holder 900 into the superior vertebral body on the anterior or lateral side of the spinal column over a bone graft. When the desired position is reached, the end user can partially engage first and second teeth 106, 108 with the bone enabling the end user to fasten a bone screw 10, 50 through the opening 102 on the plate 100 to the superior vertebral body. Consequently, the bone screw 10, 50 fastening drives first and second teeth 106, 108 farther into the bone for additional support. The end user can remove the plate holder 900 from the plate 100 by re-actuating the locked actuator 922, which disengages the pawl end 904*a* of the handle 904 from the ratchet teeth 930, enabling the compression forces from the first and second bias bars 926, 928 to springingly thrust actuator 922 and ratchet 924 forward, disengaging the rod 916 from the aperture 120. The end user can then disengage the plate holder 900 from the plate 100. As mentioned above, the bone screw 10, 50 is locked to the plate 100 to inhibit the screw 10, 50 from backing out since the material of the plate 100 is softer than the material of the screw 10, 50.

Since the first and second tooth 106, 108 provide added engaging support to the plate 100 while it is affixed to the vertebra, the end user may remove the plate holder 900 when the first and second teeth 106, 108 are partially engaged into the bone. Alternatively, the end user can remove the plate holder 900 when the plate 100 is fully fastened by the bone screw 10, 50.

It will be understood that various modifications may be made to the embodiments of the presently disclosed spinal buttress plate. Therefore, the above description should not be construed as limiting, but merely as exemplifications of embodiments. Those skilled in the art will envision other modifications within the scope and spirit of the present disclosure.

What is claimed is:

1. A buttress plate, comprising:
a screw having a head and a shank for engaging bone;
a body having a cephalad end, a caudad end, a top surface, and a bottom surface, the body defining an opening and forming an annular lip within the opening, the annular lip defined by a first frustoconical cavity having a first major diameter formed proximate the top surface of the plate and a second frustoconical cavity having a second major diameter formed proximate the bottom surface of the plate, the first and second frustoconical cavities extending into the plate such that the first and second frustoconical cavities converge at a minor diameter that is less than the first and second major diameters, the first and second frustoconical cavities having respective first and second surfaces, at least one of the first and second surfaces being non-threaded, the opening configured to receive the shank of the screw therethrough for facilitating the securement of the buttress plate to at least one vertebra, the head of the screw configured to engage the annular lip to secure the screw to the body;
a ledge defining an aperture therethrough, the aperture being enclosed within boundaries of the ledge, the ledge being disposed on at least one of the cephalad end and the caudad end of the body and extending to at least one of a cephalad-most end and a caudad-most end of the body, wherein the entire ledge is disposed medially between the top surface and the bottom surface of the body, wherein the ledge includes top and bottom surfaces that are recessed from the top and bottom surfaces of the body, respectively, such that the top and bottom surfaces of the body at least partially surround the ledge, and wherein the ledge and aperture are adapted to engage an instrument for positioning the buttress plate adjacent a spinal bone graft; and
a pair of teeth disposed in spaced-apart relation on the bottom surface of the body and positionable within the at least one vertebra.

2. The buttress plate of claim 1, wherein a portion of the top and bottom surfaces of the body are removed to integrally form the ledge within the body.

3. The buttress plate of claim 2, wherein the ledge is fixedly secured to the body.

4. The buttress plate according to claim 1, wherein the pair of teeth and the ledge are disposed on opposing ends of the body.

5. The buttress plate according to claim 1, wherein at least one tooth of the pair of teeth is mounted to the body by a footing.

6. The buttress plate according to claim 1, wherein the annular lip is formed of commercially pure titanium.

7. The buttress plate according to claim 1, wherein the annular lip has a curvaceous surface.

8. The buttress plate according to claim 1, wherein the screw is a self-tapping screw.

9. The buttress plate according to claim 1, wherein the screw is a self-starting screw.

10. The buttress plate of claim 1, wherein the entire aperture is disposed offset from caudad and cephalad-most ends of the ledge.

11. The buttress plate of claim 1, wherein the head of the screw has a first thread and the shank of the screw has a second thread, wherein the screw is formed of a first material and the body is formed of a second material that is softer than the first material of the screw, and wherein the annular lip of the body deforms as the first thread of the screw engages the annular lip to secure the head of the screw to the body.

12. The buttress plate of claim 1, wherein the annular lip is continuous and uninterrupted about the opening of the body.

13. A method of attaching a buttress plate, comprising:
mounting a rod of an instrument within an aperture of a ledge of a buttress plate wherein the entire ledge of the buttress plate is recessed from top and bottom surfaces of the buttress plate;
distally advancing the rod of the instrument relative to a prop of the instrument to support the ledge of the buttress plate against the prop of the instrument and secure the instrument to the buttress plate;
supporting the ledge of the buttress plate against the prop of the instrument;
positioning the buttress plate adjacent a superior vertebral body on at least one of the anterior or lateral sides of a spinal column over a bone graft; and securing a screw to the buttress plate by engaging a thread on a head of the screw with an annular lip of the buttress plate that is formed within an opening of the buttress plate such that the thread of the head of the screw deforms the annular lip of the buttress plate, the annular lip defined by a first frustoconical cavity having a first major diameter formed proximate the top surface of the plate and a second frustoconical cavity having a second major diameter formed proximate the bottom surface of the plate, the first and second frustoconical cavities extending into the plate such that the first and second frustoconical cavities converge at a minor diameter that is less than the first and second major diameters, the first and second frustoconical cavities having respective first and second surfaces, at least one of the first and second surfaces being unthreaded.

14. A method according to claim 13, further comprising driving a pair of teeth of the buttress plate into the superior vertebral body.

15. The method of claim 13, further including securing the buttress plate solely to a superior vertebral body of the spinal column.

16. A buttress plate system, comprising:
a screw formed of a first material, the screw having a head and a shank for engaging bone;
an instrument; and
a buttress plate formed of a second material softer than the first material of the screw, the buttress plate including:
 a body having a cephalad end, a caudad end, a top surface, and a bottom surface, the body defining an opening and forming an annular lip within the opening, the annular lip being continuous and uninterrupted about the opening, the annular lip defined by a first frustocone extending into the body from the top surface and a second frustocone extending into the body from the bottom surface, the first and second frustocones tapering towards a minor diameter between the top and bottom surfaces, the first and second frustocones having respective first and second surfaces, at least one of the first and second surfaces being an uninterrupted surface, the opening configured to receive the shank of the screw therethrough for facilitating the securement of the buttress plate to at least one vertebra, the head of the screw configured to deform the annular lip to secure the screw to the buttress plate;
 a ledge defining an enclosed aperture therethrough, the ledge being disposed on at least one of the cephalad end and the caudad end of the body and extending to at least one of a cephalad-most end and a caudad-most end of the body, wherein the entire ledge is recessed from the top surface and the bottom surface of the body, wherein the ledge of the buttress plate includes a bottom surface, the top surface of the ledge is recessed from the top surface of the body of the buttress plate and the bottom surface of the ledge is recessed from the bottom surface of the body of the buttress plate such that the top and bottom surfaced of the body at least partially surround the ledge, and wherein the ledge and aperture are adapted to engage the instrument; and
 a pair of teeth disposed in spaced-apart relation on the bottom surface of the body and positionable within the at least one vertebra;
wherein the instrument is configured and dimensioned to position the buttress plate adjacent a spinal bone graft.

17. The buttress plate system of claim 16, wherein the instrument includes a rod and a prop, the rod being distally advanceable relative to the prop to support the ledge of the buttress plate against the prop while securing the instrument to the buttress plate.

* * * * *